United States Patent [19]

Savion et al.

[11] Patent Number: 5,730,992
[45] Date of Patent: Mar. 24, 1998

[54] COMPOSITIONS FOR THE TREATMENT OF SKIN DISORDERS

[75] Inventors: Naphtali Savion, Givat Shmuel; Sara Brenner, Herzlia-Pituach, both of Israel

[73] Assignee: Ramot University Authority for Applied Research and Industrial Development, Ltd., Ramat Aviv, Israel

[21] Appl. No.: 615,266
[22] PCT Filed: Sep. 13, 1995
[86] PCT No.: PCT/US95/11678
§ 371 Date: Mar. 13, 1996
§ 102(e) Date: Mar. 13, 1996
[87] PCT Pub. No.: WO96/08248
PCT Pub. Date: Mar. 21, 1996

[30] Foreign Application Priority Data

Sep. 13, 1994 [IL] Israel ......................................... 110943

[51] Int. Cl.⁶ ..................................................... A61K 7/48
[52] U.S. Cl. ........................... 424/401; 514/460; 514/859; 514/944; 514/969
[58] Field of Search ............................. 424/401; 514/460, 514/859, 944, 969

[56] References Cited

U.S. PATENT DOCUMENTS 4,231,938  11/1980  Monaghan et al. ................. 260/343.5

OTHER PUBLICATIONS

J.S. Strauss, "The Pathogenesis of Acne: How Might Azelaic Acid Act?", Journal of Dermatological Treatment (1989) I, 3–6.

H. Gollnick, "The New Therapeutic Agent: Azelaic Acid in Acne Treatment", Journal of Dermatological Treatment (1990) 1 (Suppl 3): S23–S28.

Goldstein, Joseph L. and Brown, Michael S., "Regulation of the Mevalonate Pathway", Nature, vol. 343, 1 Feb. 1990, 425–430.

The Merck Index, An Encyclopedia of Chemicals, Drugs and Biologicals, 11th Edition, 1989.

*Primary Examiner*—Jyothsan Venkat
*Attorney, Agent, or Firm*—Wigman, Cohen, Leitner & Myers, P.C.

[57] ABSTRACT

An inhibitor of cholesterol synthesis is used for the treatment, alleviation or prevention of skin disorders.

8 Claims, No Drawings

COMPOSITIONS FOR THE TREATMENT OF SKIN DISORDERS

FIELD OF THE INVENTION

The present invention is generally in the field of compositions for topical application onto the skin intended to improve the skin's condition. The present invention provides method and compositions useful for improving various skin conditions, in particular acne.

BACKGROUND OF THE INVENTION

Acne is a chronic inflammatory disorder of the pilosebaceous follicles, particularly in the face and neck region, occurring most commonly in adolescence between the ages of about 14 to about 19. Acne involves increased sebum secretion, hyperkeratinization in the infrainfundibulum of the follicular duct, increased microbial colonization and inflammation (Strauss, J. S., *J. Dermatol. Treat.*, 1:3–6 (1989)). Various methods for the treatment of acne and other sebaceous glands' inflammation have been proposed, ranging from special diets, prevention of contact of the skin by known acneignic agents (e.g., low grade cosmetics), use of endocrine preparations containing progesterone or estrogen, and others, most of which have not proved to be effective. Additionally, it has also been proposed to use antiseptic, antibacterial and wide-spectrum antibiotic compounds in both topical and systemic application.

All hitherto used anti-acne agents were effective in suppressing the development of microbial population, keratinization and comedo formation in the sebaceous glands. However, only few of the anti-acne agents hitherto used were effective in the reduction of the sebum excretion rate (Gollnick, H., *J. Dermatol. Treat.* 1:S23–S28 (1990) and none of the agents was useful in affecting lipid biosynthesis in the pilosebaceous unit.

Isoprenoid groups such as cholesterol, squalene and cholesteryl-esters are synthesized via the mevalonate pathway (Goldstein, J. L., Brown, M. S., *Nature*, 34B, 425 (1990)), wherein the end-product is cholesterol. One of the key enzymes which regulate the production of mevalonate, the precursor of the above isoprenoid groups, is the 3-hydroxy-3-methylglutary coenzyme A (HMG-CoA) reductase. Inhibitors of this enzyme inhibit the synthesis of cholesterol and are thus used as antihypercholesterolemic medicaments for the treatment of arteriosclerosis, hyperlipemia and related diseases. An example of such an inhibitor is Lovastatin (Merck Index 5460, U.S. Pat. No. 4,231,938). Pharmaceutical compositions comprising this inhibitor of HMC-CoA reductase are given orally or parenterally to patients suffering from arteriosclerosis or hyperlipemia.

SUMMARY OF THE INVENTION

In accordance with the invention it has surprisingly been found that acne can be treated by the use of a topically applied inhibitor of cholesterol synthesis. In accordance with the invention use is thus made with an inhibitor of cholesterol synthesis to treat various skin disorders.

In accordance with the present invention there is thus provided a composition for topical skin application comprising a carrier and, as an active ingredient, an effective amount of an inhibitor of cholesterol synthesis.

The composition of the invention may be a pharmaceutical or cosmetic composition.

The pharmaceutical composition of the invention may be used for various indications including acne vulgaris, psoriasis, scalp dandruff and saborea.

The present invention further concerns the use of inhibitors of cholesterol synthesis, for example inhibitors of the HMG-CoA reductase, for the preparation of topical pharmaceutical compositions for the treatment, alleviation or prevention of skin disorders.

Also provided by the invention is a method for improvement of skin condition comprising topically applying onto the skin a composition comprising a carrier and, as an active ingredient, an effective amount of an inhibitor of cholesterol synthesis.. A particular application of the method is the treatment, alleviation or prevention of acne.

The term "effective amount" should be understood as meaning an amount of an active ingredient needed to achieve a desired therapeutic or pharmaceutical effect. For example, in a pharmaceutical composition of the invention an effective amount of an inhibitor of cholesterol synthesis is an amount which is sufficient, in the administration regimen of the pharmaceutical composition in the framework of treatment, to achieve an improvement in the skin's condition.

Inhibitors of cholesterol synthesis useful in accordance with the present invention are various agents which inhibit the production of the end product, i.e. cholesterol, or any of the intermediates of the various steps of the mevalonate pathway in which cholesterol is produced from the precursors acety CoA and acetoacetyl CoA. The inhibitors can be agents which inhibit the enzymes involved in the various steps or agents which serve as sequesters of the intermediates, both of which reduce the amount of cholesterol produced in this process.

In accordance with a preferred embodiment of the invention, the inhibitor of cholesterol synthesis is an agent which inhibits the HMG-CoA reductase, such as Lovastatin.

The concentration of the Lovastatin is preferably about 0.2–10% and most preferably about 2%.

The inhibitor of cholesterol synthesis may be applied to the skin with various other agents such as, antimicrobial agents, e.g. antibiotics, for the treatment or prevention of a secondary infection, a skin peeling agent, retin-A separately or together with resorcinol, etc.

The carrier of the composition of the present invention may be any pharmaceutically or cosmetically acceptable carrier such as, for example, ethanol, gel, liposome formulation, ointment, salve, etc.

EXAMPLES

I. Preparation of the Composition

Lovastatin capsules (Mevacor™, Merck, U.S.A.) were ground and the active ingredient was separated from the excipient by extraction with ethanol 95% and filtration to yield a 2% solution of Lovastatin in ethanol.

II. Clinical Trials

The efficacy of the above preparation was tested in two separate clinical trials.

A. Trial I

Pharmaceutical compositions prepared as described above were topically applied twice daily for a period of 12 weeks, to the faces of two individuals suffering from acne vulgaris. The patients were required to discontinue all other topical and systemic anti-acne treatment 30 days prior to the beginning of the trial and discontinued all facial and cosmetic treatment seven days prior to the onset of treatment.

The acne condition was assessed by recording all acne lesions including inflamed acne lesions (papules and pustules) and non-inflamed acne lesions, (white and black comedos) prior to the beginning of treatment and 4, 8 and 12 weeks following the onset of treatment.

In both patients, improvement in all mentioned lesions was noticed and at the end of the 12 week treatment period the number of lesions decreased to less than half. No side effects were noticed save for a mild dryness of the skin, which is likely a result of the ethanol.

B. Trial II 4 patients, 16–25 years of age, consisting of 2 males and 2 females, having mild to moderate acne were treated with the above preparation. All medications and cosmetics were stopped for 14 days, following which the patients were asked to apply the preparation twice daily for 8 weeks and to refrain from using all other forms of treatment and cosmetics during treatment. Prior to and after 4 and 8 weeks of treatment, the number of acne lesions (papules, pustules and white and black comedos) was recorded, and the results, shown in the following Table 1 demonstrated an improvement in all 4 patients evidenced by reduction of the number of all types of lesions:

TABLE 1

Number of acne lesions before and during treatment

| Patient | Lesions | Before Treatment | After 1 month | After 2 months |
|---|---|---|---|---|
| 1 | Pustules | 10 | 7 | 3 |
|   | Papules | 11 | 3 | 2 |
|   | White & blackheads | 18 | 10 | 7 |
| 2 | Pustules | 17 | 15 | 2 |
|   | Papules | 17 | 15 | 10 |
|   | White & blackheads | 18 | 15 | 6 |
| 3 | Pustules | 7 | 2 | — |
|   | Papules | 12 | 7 | 4 |

TABLE 1-continued

Number of acne lesions before and during treatment

| Patient | Lesions | Before Treatment | After 1 month | After 2 months |
|---|---|---|---|---|
|   | White & blackheads | 22 | 14 | 7 |
| 4 | Pustules | 20 | 18 | 5 |
|   | Papules | 16 | 9 | 5 |
|   | White & blackheads | 15 | 10 | 5 |
| Average | Pustules | 13 | 10 | 2 |
|   | Papules | 14 | 8 | 5 |
|   | White & blackheads | 18 | 12 | 6 |

What is claimed is:

1. A method for treating acne comprising the step of applying to the skin a pharmaceutically effective amount of an inhibitor of HMG-CoA reductase.

2. The method of claim 16 wherein said inhibitor is Lovastatin.

3. A method according to claim 1 comprising:

(a) said inhibitor in a concentration of about 0.2–10% and (b) a carrier for topical application to the skin.

4. The method of claim 3 wherein said carrier is a gel.

5. The method of claim 3 wherein said carrier is an ointment.

6. The method of claim 3 wherein said carrier is a salve.

7. The method of claim 3 wherein said inhibitor is in a concentration of about 2%.

8. The method of claim 3 and further comprising an anti-acne agent selected from the group consisting of antimicrobial agents, peeling agents and retinoeids.

* * * * *

UNITED STATES PATENT AND TRADEMARK OFFICE
CERTIFICATE OF CORRECTION

PATENT NO. : 5,730,992
DATED : March 24, 1998
INVENTOR(S) : Naphtali SAVION et al.

It is certified that error appears in the above-indentified patent and that said Letters Patent is hereby corrected as shown below:

Column 1, line 38, change "34B" to --343--;

Column 1, line 45, change "methylglutary" to --methylglutaryl--;

Column 1, line 49, change "HMC" to --HMC--;

Column 1, line 56, change "invention use is thus made with an inhibitor" to --invention it is thus proposed to use an inhibitor--;

Column 1, last line, delete the word "psoriasis";

Column 1, last line, change "saborea" to --seborrhea--;

Column 2, line 10; after the word "synthesis" delete the unnecessary full stop;

Column 4, claim 2, change "claim 16" to read --claim 1 --.

Signed and Sealed this

Twenty-second Day of September, 1998

Attest:

BRUCE LEHMAN

Attesting Officer

Commissioner of Patents and Trademarks